US008669273B2

(12) United States Patent
Zacharchuk et al.

(10) Patent No.: US 8,669,273 B2
(45) Date of Patent: Mar. 11, 2014

(54) ANTINEOPLASTIC COMBINATIONS OF 4-ANILINO-3-CYANOQUINOLINES AND CAPECITABINE

(75) Inventors: Charles Michael Zacharchuk, Westford, MA (US); Susan Elizabeth Quinn, Norwood, MA (US); Kenneth Kuan-Yuen Wang, Waltham, MA (US); Florence Marie Helene Binlich, Ville d'Avray (FR)

(73) Assignee: Wyeth LLC, Madison, NJ (US)

( * ) Notice: Subject to any disclaimer, the term of this patent is extended or adjusted under 35 U.S.C. 154(b) by 713 days.

(21) Appl. No.: 12/534,895

(22) Filed: Aug. 4, 2009

(65) Prior Publication Data

US 2010/0113474 A1    May 6, 2010

Related U.S. Application Data

(60) Provisional application No. 61/085,913, filed on Aug. 4, 2008, provisional application No. 61/172,466, filed on Apr. 24, 2009.

(51) Int. Cl.
*A61K 31/47* (2006.01)
*A61K 31/505* (2006.01)
(52) U.S. Cl.
USPC ........................................ 514/312; 514/274
(58) Field of Classification Search
USPC .................................................. 514/274, 312
See application file for complete search history.

(56) References Cited

U.S. PATENT DOCUMENTS

| 4,966,891 | A | 10/1990 | Fujiu et al. |
| 5,453,497 | A | 9/1995 | Kamiya et al. |
| 5,472,949 | A | 12/1995 | Arasaki et al. |
| 5,476,932 | A | 12/1995 | Brinkman et al. |
| 6,002,008 | A | 12/1999 | Wissner et al. |
| 6,288,082 | B1 | 9/2001 | Wissner et al. |
| 6,297,258 | B1 | 10/2001 | Wissner et al. |
| 6,780,996 | B2 | 8/2004 | Boschelli et al. |
| 7,297,795 | B2 | 11/2007 | Sutherland et al. |
| 7,399,865 | B2 | 7/2008 | Wissner et al. |
| 2005/0059678 | A1 | 3/2005 | Wissner et al. |
| 2006/0178387 | A1* | 8/2006 | Fujimoto-Ouchi et al. .. 514/269 |
| 2007/0104721 | A1 | 5/2007 | Moore et al. |

FOREIGN PATENT DOCUMENTS

| WO | WO 96/33978 | 10/1996 |
| WO | WO 96/33980 | 10/1996 |
| WO | 2005/018677 A2 | 3/2005 |
| WO | 2006/081985 A1 | 8/2006 |
| WO | 2006/113151 A2 | 10/2006 |
| WO | 2006/120557 A1 | 11/2006 |
| WO | 2007056118 A1 | 5/2007 |
| WO | 2008/076143 A1 | 6/2008 |
| WO | 2009/042613 A1 | 4/2009 |

OTHER PUBLICATIONS

Walko et al. Clinical Therapeutics, 2005, vol. 27, pp. 23-44.*
Twelves et al. Eur. J. Cancer, Feb. 2008, vol. 44, No. 3, pp. 419-426.*
Rabindran et al. Cancer Res., 2004, vol. 64, pp. 3958-3965.*
Reid et al. Eur. J. Cancer, Feb. 2007, vol. 43, pp. 481-489.*
Meyerhardt et al. J. Clin. Oncol., 2006, vol. 24, No. 12, pp. 1892-1897.*
F.-Ouchi et al. Cancer Chemother. Pharmacol., 2006, vol. 57, pp. 693-702.*
Parkin, D.M., Fernandez, L.M., "Use of Statics to Assess the Global Burden of Breast Cancer," Breast Journal; Jan.-Feb. 2006; 12 Suppl 1:570-80.
Smith, I., "Goals of Treatment for Patients ith Metastatic Breast Cancer," Seminars in Oncology; Feb. 2006; 33(1 Suppl 2):S2-5.
Pegram, M.D., et al.,"The Molecular and Cellular Biology of HER2/neu Gene Amplification/Overexpression and the Clinical Development of Herceptin (Trastuzumab) Therapy for Breast Cancer," Cancer Treatment and Research; 2000;103:57-75.
Xia, W., "Truncated ErbB2 Receptor (p95ErbB2) is Regulated by Heregulin through Heterodimer Formation with ErbB3 Yet Remains Sensitive to the Dual EGFR/ErbB2 Kinase Inhibitor GW572016," Oncogene 2004; 23:646-653.
Rampaul, R.S., et al., "Clinical Value of Epidermal Growth Factor Receptor Expression in Primary Breast Cancer," Adv. Anat. Pathol.; 2005; 12:271-273.
Zaczek, A., et al., "The Diverse Signaling Network of EGFR, HER2, HER3 and HER4 Tyrosine Kinase Receptors and the Consequences for Therapeutic Approaches," Histol. Histopathol.; 2005; 20:1005-1015.
Remington's Pharmaceutical Sciences, 17th Edition, ed. Alfonso R. Gennaro, Mack Publishing Company, Easton, PA (1985).
Al-Muhammed, J. Microencapsul., 13:293-306, 1996.
Chonn, Curr. Opin. Biotechnol., 6:698-708, 1995.
Ostro, Am. J. Hosp. Pharm., 46:1576-1587, 1989.
Rao, J. Biomater Sci. Polym. Ed., 7:623-645, 1995.
Gao, Pharm. Res., 12:857-863, 1995.
Eyles, J. Pharm. Pharmacol., 49:669-674, 1997.
Burstein, H.J., Awada, A., Badwe, R., et al.; 2007 Poster presented at the SABCS, San Antonio, USA.
Saura et al., "Safety and efficacy of neratinib in combination with capecitabine in patients with ErbB2-positive breast cancer," Thirty-Fourth Annual CTRC-AACR San Antonio Breast Cancer Symposium, Dec. 6-10, 2011, Abstract # P1-12-09.
Nole et al., "Dose-finding and pharmacokinetic study of an all-oral combination regimen of oral vinorelbine and capecitabine for patients with metastatic breast cancer," Ann. Oncol., 2006, 17, 322-329.
Geyer et al., "Lapatinib plus capecitabine for HER2-positive advanced breast cancer," N. Engl. J. Med., 2006, 355, 2733-2743.

(Continued)

*Primary Examiner* — James D Anderson
(74) *Attorney, Agent, or Firm* — Jones Day

(57) ABSTRACT

A combination of a 4-anilino-3-cyanoquinoline compound (e.g. HKI-272, SKI-606, EKB-569) and a capecitabine compound in the treatment of a neoplasm is provided. Regimens, kits, and methods for treatment of neoplasm, including breast cancer including metastatic breast cancer, and lung cancer, using this combination, optionally in combination with other anti-neoplastic agents, or immune modulators are also described.

23 Claims, No Drawings

(56) References Cited

OTHER PUBLICATIONS

Jallal et al., "A Src/Abl kinase inhibitor, SKI-606, blocks breast cancer invasion, growth, and metastasis in vitro and in vivo," Cancer Res., 2007, 67, 1580-1588.
Lorusso et al., "Therapeutic potential of novel selective-spectrum kinase inhibitors in oncology," Expert Opin. Investig. Drugs, 2008, 17, 1013-1028.
Boyd et al., "Lapatanib: Oncolytic dual EFGR and erbB-2 inhibitor," Drugs of the Future, 2005, 30, 1225-1239.
Heymach et al., "Epidermal growth factor receptor inhibitors in development for the treatment of non-small cell lung cancer," Clin. Cancer Res., 2006, 12, 4441s-4445s.
Ocana et al., "Identifying breast cancer druggable oncogenic alternations: Lessons learned and future targeted options," Clin. Cancer Res., 2008, 14, 961-970.
Jackisch, "Challenges in the treatment of ErbB2 (HER2)-positive breast cancer," EJC Supplements, Jun. 7-14, 2008.

* cited by examiner

ANTINEOPLASTIC COMBINATIONS OF 4-ANILINO-3-CYANOQUINOLINES AND CAPECITABINE

CROSS-REFERENCE TO RELATED APPLICATIONS

This application claims the benefit under 35 U.S.C. §119 (e) to U.S. Provisional Application Ser. No. 61/085,913, filed Aug. 4, 2008 and U.S. Provisional Application Ser. No. 61/172,466, filed Apr. 24, 2009, which are hereby incorporated by reference in their entirety.

BACKGROUND OF THE INVENTION

Breast cancer is the most frequently diagnosed malignancy in women and one of the top two causes of cancer-related deaths in women worldwide [Parkin D M, Fernandez L M. Use of statistics to assess the global burden of breast cancer. *Breast Journal*. January-February 2006; 12 Suppl 1:S70-80]. The incidence of breast cancer is estimated to reach 5 million women in the next decade.

Among women with primary breast cancer, 40 to 50% will develop metastatic disease, which despite active cytotoxic chemotherapy and newer biologic agents remains incurable [Smith I. Goals of treatment for patients with metastatic breast cancer. *Seminars in Oncology*. February 2006; 33(1 Suppl 2):S2-5]. As a result, treatment is aimed at palliation and improved quality of life, inhibition of disease progression and improvement in survival time.

The erythroblastic leukemia viral oncogene homolog (erb) family of tyrosine kinase inhibitors (TKIs) consists of 4 members: erbB-1 (EGFR [epidermal growth factor receptor]), erbB-2 (HER2, neu), erbB-3 (HER3) and erbB-4 (HER4). The erbB family of receptors is involved in cell proliferation, tumorigenesis, and metastasis and is abnormally expressed in multiple tumor types. The oncogenic role of erbB-2 has been most extensively documented in breast cancer, where gene amplification (as measured by positive fluorescence in situ hybridization [FISH]) or overexpression (as measured by immunohistochemistry [IHC] 3+) occurs in 25%-30% of breast cancers. Subjects with erbB-2-overexpressing breast cancers have been associated with more aggressive disease and poorer prognosis than for subjects whose tumors do not overexpress erbB-2 [Pegram M D, et al., The molecular and cellular biology of HER2/neu gene amplification/overexpression and the clinical development of herceptin (trastuzumab) therapy for breast cancer. *Cancer Treatment & Research*. 2000; 103:57 75].

Many different cytotoxic agents are currently available for the treatment of metastatic breast cancer (MBC), and multiple factors determine the choice of treatment. These include previous adjuvant therapy, tumor characteristics, subject characteristics, and subject preference. As anthracycline and taxanes are the most active cytotoxic agents in breast cancer, anthracycline/taxane-containing regimens are the mainstay of adjuvant therapy.

Capecitabine has been on the market since 1998, when it was the first oral chemotherapy approved by the FDA for the treatment of metastatic breast cancer [FDA. Prescribing Information for Xeloda® (capecitabine) U.S. Government; 2006]. Capecitabine (5'-deoxy-5-fluoro-N-[(pentyloxy)carboyl]-cytidine) is a fluoropyidine carbamate analog with anti-tumor activity. Capecitabine is used as monotherapy and in combination therapy regimens for the treatment and palliative management of various forms of cancer including colorectal and breast cancer. Despite its demonstrated clinical usefulness, there are a number of disadvantages associated with the use of capecitabine which can be dose-limiting and which may render patients unable to tolerate treatment using capecitabine. Adverse reactions commonly seen during systemic therapy using capecitabine, include diarrhea, stomatitis, nausea and vomiting, hand-and-foot syndrome, anemia, hyperbilirubinemia, dermatitis and alopecia. Other adverse effects associated with the systemic administration of capecitabine include constipation, abdominal pain, edema, decrease appetite, dyspnea, back pain, neutropenia, nail disorders, pyrexia, asthenia, fatigue, weakness, headache dizziness, anorexia, arthralgia, myalgia, neutropenic fever, cough, sore throat, leukopenia and thrombocytopenia.

The use of the antibody trastuzumab for breast cancer treatment has been described. However, breast cancer cells may become resistant to trastuzumab on the basis of extracellular domain (ECD) truncated erbB-2 receptor, that can no longer be recognized by the antibody [Xia, W. Truncated ErbB2 receptor (p95ErbB2) is regulated by heregulin through heterodimer formation with ErbB3 yet remains sensitive to the dual EGFR/ErbB2 kinase inhibitor GW572016. *Oncogene* 2004, 23:646-653], or because of coactivation of erbB-1 signaling [Rampaul, R S, et al, Clinical value of epidermal growth factor receptor expression in primary breast cancer. *Adv Anat Pathol* 2005, 12:271-273; Zaczek, A, et al., The diverse signaling network of EGFR, HER2, HER3 and HER4 tyrosine kinase receptors and the consequences for therapeutic approaches. *Histol Histopathol* 2005, 20:1005-1015].

What are needed are additional effective therapies for solid tumors and/or breast cancer.

SUMMARY OF THE INVENTION

In one aspect, a combination therapy for an Erb-1 overexpressing (amplified) and/or an Erb-2-overexpressing (amplified) neoplasm is provided. This combination therapy comprises a regimen involving the two anti-neoplastic agents HKI-272 (neratinib) and capecitabine.

In another aspect, a combination therapy for treatment of a solid tumor neoplasm in a subject is provided which includes administering HKI-272 and administering capecitabine.

In still another aspect, a combination therapy is useful for treatment of breast cancer.

In yet another aspect, the combination therapy is utilized for treatment of ErbB-2 positive metastatic or locally advanced breast cancer is provided. This combination therapy comprises delivering a combination of HKI-272 and capecitabine.

In yet a further aspect, a pharmaceutical pack for treating a neoplasm in one individual mammal is provided and includes (a) at least one unit dose of capecitabine; and (b) at least one unit dose of HKI-272.

In another aspect, a pharmaceutical composition is described and contains capecitabine, HKI-272, and at least one pharmaceutically acceptable carrier.

In still another aspect, a method of treating a neoplasm associated with overexpression or amplification of Erb-1 and/or Erb-2 in a mammal in need thereof is provided and includes administering a unit dose of a capecitabine compound and administering a unit dose of a HKI-272 compound.

In a separate aspect, a combination therapy for an Erb-1 overexpressing (amplified) and/or an Erb-2-overexpressing (amplified) neoplasm is provided. This combination therapy comprises a regimen involving the two anti-neoplastic agents SKI-606 (bosutinib) and capecitabine.

In another aspect, a combination therapy for treatment of a solid tumor neoplasm in a subject is provided which includes administering SKI-606 (Bosutinib) and administering capecitabine.

In still another aspect, a combination therapy is useful for treatment of breast cancer.

In yet another aspect, the combination therapy is utilized for treatment of ErbB-2 positive metastatic or locally advanced breast cancer is provided. This combination therapy comprises delivering a combination of SKI-606 and capecitabine.

In yet a further aspect, a pharmaceutical pack for treating a neoplasm in one individual mammal is provided and includes (a) at least one unit dose of capecitabine; and (b) at least one unit dose of SKI-606.

In another aspect, a pharmaceutical composition is described and contains capecitabine, SKI-606, and at least one pharmaceutically acceptable carrier.

In still another aspect, a method of treating a neoplasm associated with overexpression or amplification of Erb-1 and/or Erb-2 in a mammal in need thereof is provided and includes administering a unit dose of a capecitabine compound and administering a unit dose of a SKI-606 compound.

Other aspects and advantages of the invention will be readily apparent from the following detailed description of the invention.

DETAILED DESCRIPTION OF THE INVENTION

An anti-neoplastic regimen utilizing the two active components neratinib (HKI-272) and capecitabine are described. This regimen is particularly well suited for treatment of Erb-2 (HER-2)-associated neoplasms. In another embodiment, this regimen is used for the treatment of Erb-1-associated neoplasms. In one embodiment, these two components are the sole anti-neoplastic components in the regimen. In another embodiment, the regimen further involves delivery of other active agents, which are non-antineoplastic.

As used herein, "a HKI-272 compound" refers, in one embodiment, to a compound having the following core structure:

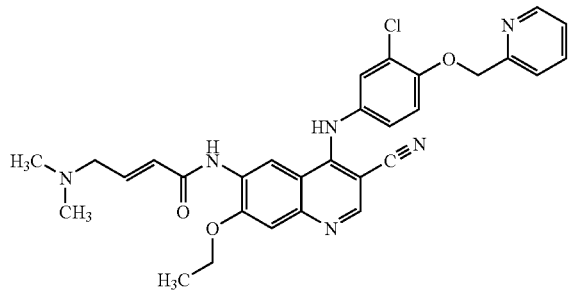 [SMILES: CCOc1cc2ncc(C#N)c(Nc3ccc(OCc4ccccn4)c(Cl)c3)c2cc1NC(=O)/C=C/CN(C)C]

or a derivative or pharmaceutically acceptable salt thereof. Suitable derivatives may include, e.g., an ester, ether, or carbamate. The core structure represented above is a particularly HKI-272 compound, called HKI-272 or neratinib, which has the chemical name [(2E)-N-[4-[[3-chloro-4-[(pyridin-2-yl)methoxy]phenyl]amino]-3-cyano-7-ethoxyquinolin-6-yl]-4-(dimethylamino)but-2-enamide]. In one embodiment, the HKI-272 compound useful in the compositions and methods described herein is HKI-272.

In another embodiment, an HKI-272 compound has the structure:

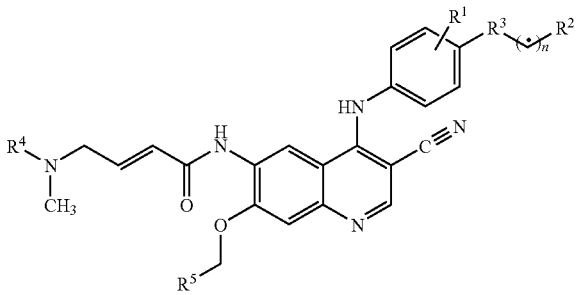

wherein:
$R^1$ is halogen;
$R^2$ is pyridinyl, thiophenyl, pyrimidinyl, thiazolyl, or phenyl, wherein $R^2$ is optionally substituted with up to three substituents;
$R^3$ is O or S;
$R^4$ is $CH_3$ or $CH_2CH_2OCH_3$;
$R^5$ is $CH_3$ or $CH_2CH_3$; and
n is 0 or 1.

The term "halogen" as used herein refers to Cl, Br, I, and F.

These HKI-272 compounds, of which HKI-272 is a species, are characterized by the ability to act as potent HER-2 inhibitors, as disclosed in U.S. Pat. Nos. 6,288,082 and 6,297,258 and U.S. Patent Application Publication No. 2007/0104721. These compounds and their preparation are described in detail in U.S. Patent Application Publication No. 2005/0059678. For convenience, "a HKI-272 compound" is used throughout this specification. However, in another embodiment, another compound of the structure(s) provided above is substituted for HKI-272 in one or more of the combinations described in detail below.

HKI-272, other HKI-272 compounds, and methods of making and formulating same have been described in, for example, U.S. Patent Application Publication No. 2005/0059678 and U.S. Pat. No. 6,002,008. The methods described in these documents can also be used to prepare the substituted 3-quinoline compounds used herein and are hereby incorporated by reference. In addition to the methods described in these documents, International Patent Publication Nos. WO-96/33978 and WO-96/33980, describe methods that are useful for the preparation of these HKI-272 compounds. Although these methods describe the preparation of certain quinazolines, they are also applicable to the preparation of correspondingly substituted 3-cyanoquinolines and are hereby incorporated by reference.

The chemical name for capecitabine is 5'-deoxy-5-fluoro-N-[(pentyloxy)-carbonyl]-cytidine. Capecitabine is covered in U.S. patents, including U.S. Pat. Nos. 4,966,891 and 5,472,949. Capecitabine is currently commercially available as XELODA® [ROCHE]. Methods for the manufacture of capecitabine are taught in U.S. Pat. Nos. 5,453,497 and 5,476,932. To the extent necessary, any and all of the foregoing patents and applications are used in accordance with the invention as disclosed.

The HKI-272 and capecitibine compounds and corresponding pharmaceutically acceptable salts or esters thereof include isomers either individually or as a mixture, such as enantiomers, diastereomers, and positional isomers.

An anti-neoplastic regimen utilizing the two active components bosutinib (SKI-606) and capecitabine are described. This regimen is particularly well suited for treatment of Erb-2 (HER-2)-associated neoplasms. In another embodiment, this regimen is used for the treatment of Erb-1-associated neoplasms. In one embodiment, these two components are the sole anti-neoplastic components in the regimen. In another embodiment, the regimen further involves delivery of other active agents, which are non-antineoplastic.

As used herein, SKI-606 refers, in one embodiment, to a Src inhibitor compound having the following core structure:

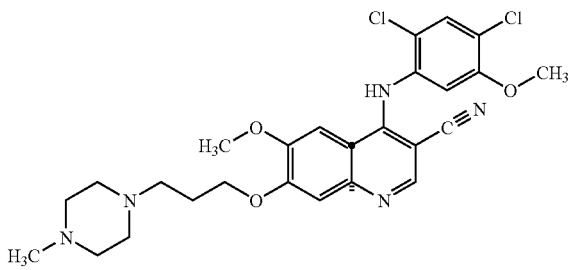

or a derivative or pharmaceutically acceptable salt thereof. Suitable derivatives may include, e.g., an ester, ether, or carbamate. The core structure represented above is called SKI-606 or bosutinib, which has the chemical name 4-(2,4-dichloro-5-methoxy-phenylamino)-6-methoxy7-[3-(4-methyl-piperizin-1-yl)-propoxy]-quinoline-3-carbonitrile). Other 4-anilino-3-cyanoquinolines are described in U.S. Pat. Nos. 6,002,008; 6,288,082; 6,297,258; 6,780,996; 7,297,795 and 7,399,865.

The SKI-606 and capecitibine compounds and corresponding pharmaceutically acceptable salts or esters thereof include isomers either individually or as a mixture, such as enantiomers, diastereomers, and positional isomers.

"Pharmaceutically acceptable salts and esters" refers to salts and esters that are pharmaceutically acceptable and have the desired pharmacological properties. Such salts include, e.g., salts that can be formed where acidic protons present in the compounds are capable of reacting with inorganic or organic bases. Suitable inorganic salts include, e.g., those formed with the alkali metals or alkaline earth metals, e.g. sodium, potassium, magnesium, calcium, aluminum. Suitable organic salts also include, e.g., those formed with organic bases such as the amine bases, e.g., ethanolamine, diethanolamine, triethanolamine, tromethamine, N-methylglucamine, and the like, and those which can form N-tetraalkylammonium salts such as N-tetrabutylammonium salts. Pharmaceutically acceptable salts can also include acid addition salts formed from the reaction of basic moieties, such as amines, in the parent compound with inorganic acids (e.g., hydrochloric and hydrobromic acids) and organic acids (e.g., acetic acid, citric acid, maleic acid, propionic, lactic, tartaric, succinic, fumaric, maleic, malonic, mandelic, malic, phthalic, hydrochloric, hydrobromic, phosphoric, nitric, sulfuric, and the alkane- and arene-sulfonic acids such as methanesulfonic acid and benzenesulfonic acid naphthalenesulfonic, toluenesulfonic, camphorsulfonic). Other suitable examples of pharmaceutically acceptable salts include, but are not limited to sulfate; citrate, acetate; oxalate; chloride; bromide; iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucaronate; saccharate; formate; benzoate; glutamate; methanesulfonate; ethanesulfonate; benzenesulfonate; p-toluenesulfonate; pamoate (i.e., 1,1'-methylene-bis-(2-hydroxy-3-naphthoate)); and salts of fatty acids such as caproate, laurate, myristate, palmitate, stearate, oleate, linoleate, and linolenate salts.

Pharmaceutically acceptable esters include esters formed from carboxy, sulfonyloxy, and phosphonoxy groups present in the compounds of the invention, e.g., straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds utilized herein may be present in unsalified or unesterified form, or in salified and/or esterified form, and the naming of such compounds is intended to include both the original (unsalified and unesterified) compound and its pharmaceutically acceptable salts and esters. Also, one or more compounds utilized herein may be present in more than one stereoisomeric form, and the naming of such compounds is intended to include all single stereoisomers and all mixtures (whether racemic or otherwise) of such stereoisomers.

According to one embodiment, the use the combination HKI-272 and the capecitabine compound for the treatment of neoplasms is provided. In one embodiment, the neoplasm is an Erb-2 associated or overexpressing neoplasm. In one embodiment, the neoplasm is a breast cancer. For example, the breast cancer can be an Erb-2 positive metastatic breast cancer or a locally advanced breast cancer. In another embodiment, the neoplasm is an Erb-2 positive solid tumor.

According to a separate embodiment, the use the combination SKI-606 and the capecitabine compound for the treatment of neoplasms is provided. In one embodiment, the neoplasm is an Erb-2 associated or overexpressing neoplasm. In one embodiment, the neoplasm is a breast cancer. For example, the breast cancer can be an Erb-2 positive metastatic breast cancer or a locally advanced breast cancer. In another embodiment, the neoplasm is an Erb-2 positive solid tumor.

As used herein, the term "effective amount" or "pharmaceutically effective amount" when administered to a subject to treat a neoplasm, is sufficient to inhibit, slow, reduce, or eliminate lesions or tumor growth in a subject, or to inhibit, slow, or reduce progression of disease and/or to increase progression-free survival rate of the subject.

According to one embodiment, use of a combination of the HKI-272 compound and capecitabine compound also provides for the use of combinations in which the HKI compound and/or the capecitabine compound is used at a subtherapeutically effective dosage. A subtherapeutically effective dosage refers to a dose lower than the amount which is effective when the drug is delivered alone (monotherapy). Although less desirable, it is possible that one of the active agents may be used in a supratherapeutic amount, i.e., at a higher dosage in the combination than when used alone. In this embodiment, the other active agent(s) may be used in a therapeutic or subtherapeutic amount.

According to a separate embodiment, use of a combination of the SKI-606 compound and capecitabine compound also provides for the use of combinations in which the Src inhibitor compound and/or the capecitabine compound is used at a subtherapeutically effective dosage. A subtherapeutically effective dosage refers to a dose lower than the amount which is effective when the drug is delivered alone (monotherapy). Although less desirable, it is possible that one of the active agents may be used in a supratherapeutic amount, i.e., at a higher dosage in the combination than when used alone. In this embodiment, the other active agent(s) may be used in a therapeutic or subtherapeutic amount.

The term "treating" or "treatment" refers to the administration of the 4-anilino-3-cyanoquinoline compound (e.g. HKI-272, SKI-606, EKB-569) and capecitabine compounds to a subject to prevent or delay, to alleviate, or to arrest or inhibit development of the symptoms or conditions associated with neoplasms.

As used herein, neoplasms which amplify/overexpress erB-2 (used interchangeably with Her-2 and neu) include certain breast cancers. Other neoplasms in which erb-2 is amplified or overexpressed may include, ovarian, bladder, gastric, pancreatic, colorectal, prostate, and lung cancers, including non-small cell lung cancers.

Neoplasms in which ErbB1 is expressed or overexpressed include a variety of solid human tumors, including non-small cell lung (NSCL), prostate, breast, colorectal, and ovarian cancers. Methods for screening samples to determine if the neoplasm overexpresses erb-1 and/or erB-2/Her-2 are known to those of skill in the art.

As used herein, the term "providing" with respect to providing a 4-anilino-3-cyanoquinoline compound (e.g. HKI-272, SKI-606, EKB-569) and a capecitabine compound, means either directly administering said compound and capecitabine compound, or administering a prodrug, derivative, or analog which will form an effective amount of said compound and/or capecitabine compound within the body.

As used herein and except where noted, the terms "individual", "subject" and "patient" are used interchangeably, and refer to any animal, including mammals, preferably mice, rats, other rodents, rabbits, dogs, cats, swine, cattle, sheep, horses, non-human primates, and humans. Desirably, the term "individual", "subject" or "patient" refers to a human. In most embodiments, the subjects or patients are in need of the therapeutic treatment. Accordingly, the term "subject" or "patient" as used herein means any mammalian patient or subject to which the 4-anilino-3-cyanoquinoline compound (e.g. HKI-272, SKI-606, EKB-569) and capecitabine compounds can be administered.

Regimen Using the HKI-272 Compound and Capecitabine Compound

As used herein, the components of the therapeutic combined regimen, i.e., the HKI-272 compound and the capecitabine compound, can be administered simultaneously. Alternatively, the two components can be administered in a staggered regimen, i.e., with the HKI-272 compound being given at a different time during the course of the cycle than the capecitabine compound. This time differential may range from several minutes, hours, days, weeks, or longer between administration of the at least two agents. Therefore, the term combination (or combined) does not necessarily mean administered at the same time or as a unitary dose or single composition, but that each of the components are administered during a desired treatment period. The agents may also be administered by different routes. In one embodiment, 1 "cycle" includes 21 days (3 weeks).

These regimens or cycles may be repeated, or alternated, as desired. Other dosage regimens and variations are foreseeable, and are determined through physician guidance.

In one embodiment, the capecitabine is administered at least once over a period of 21 days. More desirably, the capecitabine is administered daily for 14 days over a period of 21 days. Typically, a regimen involves repeating this dosage for 3 to 6 cycles.

In one embodiment, the capecitabine and/or HKI-272 compound is administered only once in the treatment. In another embodiment, the capecitabine and/or HKI-272 compound is administered at least once over a period of 21 days. In a further embodiment, the capecitabine and/or HKI-272 compound is administered at least twice over a period of 21 days. In still another embodiment, the capecitabine and/or HKI-272 compound is administered on days 1, 2, 3, 4, 5, 6, 7, 8, 9, 10, 11, 12, 13, 14, 15, 16, 17, 18, 19, 20, and/or 21 of the cycle.

In still a further embodiment, the capecitabine and/or HKI-272 compound is administered at least once daily. In yet another embodiment, the capecitabine and/or HKI-272 compound HKI-272 compound is administered on day 1. In still a further embodiment, the HKI-272 compound is administered orally at least once a day. In another embodiment, the HKI-272 compound is administered at least 1, 2, 3, or 4 times a day. In a further embodiment the capecitabine compound is administered 1, 2, 3 or 4 times a day.

In one embodiment, a single loading dose of the capecitabine compound and/or HKI-272 compound is administered. The single loading dose of the capecitabine compound and/or the HKI-272 compound may be the same dose as the subsequent doses or the single loading dose may be greater than the dose administered to the patient throughout the remaining treatment. In a further embodiment, the capecitabine compound/or the HKI-272 compound may be administered at a larger dose only once per cycle, i.e., one day per cycle.

Single doses and multiple doses of the HKI-272 and/or the capecitabine are contemplated. These compounds may be separately formulated in combination with one or more pharmaceutically acceptable carrier(s) and excipients.

Regimen Using the SKI-606 and Capecitabine

As used herein, the components of the therapeutic combined regimen, i.e., the SKI-606 compound and the capecitabine compound, can be administered simultaneously. Alternatively, the two components can be administered in a staggered regimen, i.e., with the SKI-606 compound being given at a different time during the course of the cycle than the capecitabine compound. This time differential may range from several minutes, hours, days, weeks, or longer between administration of the at least two agents. Therefore, the term combination (or combined) does not necessarily mean administered at the same time or as a unitary dose or single composition, but that each of the components are administered during a desired treatment period. The agents may also be administered by different routes. In one embodiment, 1 "cycle" includes 21 days (3 weeks).

These regimens or cycles may be repeated, or alternated, as desired. Other dosage regimens and variations are foreseeable, and are determined through physician guidance.

In one embodiment, the capecitabine is administered at least once over a period of 21 days. More desirably, the capecitabine is administered daily for 14 days over a period of 21 days. Typically, a regimen involves repeating this dosage for 3 to 6 cycles.

In one embodiment, the capecitabine and/or SKI-606 compound is administered only once in the treatment. In another embodiment, the capecitabine and/or SKI-606 compound is administered at least once over a period of 21 days. In a further embodiment, the capecitabine and/or SKI-606 compound is administered at least twice over a period of 21 days. In still another embodiment, the capecitabine and/or SKI-606 compound is administered on days 1, 2, 3, 4, 5, 6, 7, 8, 9, 10, 11, 12, 13, 14, 15, 16, 17, 18, 19, 20, and/or 21 of the cycle.

In still a further embodiment, the capecitabine and/or SKI-606 compound is administered at least once daily. In yet another embodiment, the capecitabine and/or SKI-606 compound SKI-606 compound is administered on day 1. In still a further embodiment, the SKI-606 compound is administered orally at least once a day. In another embodiment, the SKI-606 compound is administered at least 1, 2, 3, or 4 times a day.

In a further embodiment the capecitabine compound is administered 1, 2, 3 or 4 times a day.

In one embodiment, a single loading dose of the capecitabine compound and/or SKI-606 compound is administered. The single loading dose of the capecitabine compound and/or the SKI-606 compound may be the same dose as the subsequent doses or the single loading dose may be greater than the dose administered to the patient throughout the remaining treatment. In a further embodiment, the capecitabine compound/or the SKI-606 compound may be administered at a larger dose only once per cycle, i.e., one day per cycle.

Single doses and multiple doses of the SKI-606 and/or the capecitabine are contemplated. These compounds may be separately formulated in combination with one or more pharmaceutically acceptable carrier(s) and excipients.

In one embodiment, suitable examples of pharmaceutical carriers used herein include, but are not limited to, excipients, diluents, fillers, disintegrants, lubricants and other agents that can function as a carrier. The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. Pharmaceutical compositions are prepared in accordance with acceptable pharmaceutical procedures, such as described in Remingtons Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable. Suitable pharmaceutically-acceptable excipients or carriers for a tablet or caplet formulation include, e.g., inert excipients such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl 4-hydroxybenzoate, and anti-oxidants, such as ascorbic acid. Tablet or caplet formulations may be uncoated or coated either to modify their disintegration and the subsequent absorption of the active ingredient within the gastrointestinal tract, or to improve their stability and/or appearance using conventional coating agents and procedures well known in the art.

According to one embodiment, the HKI-272 compound can be administered, e.g., orally, at a dose range of about 0.01 to 100 mg/kg. In one embodiment, the HKI-272 compound is administered at a dose range of about 0.1 to about 90 mg/kg. In another embodiment, the HKI-272 compound is administered at a dose range of about 1 to about 80 mg/kg. In a further embodiment, the HKI-272 compound is administered at a dose range of about 10 to about 70 mg/kg. In yet another embodiment, the HKI-272 compound is administered at a dose range of about 15 to about 60 mg/kg. In still a further embodiment, the HKI-272 compound is administered at a dose range of about 20 to about 240 mg per day, at least about 40 mg, at least about 120 mg, or at least about 160 mg, on the days in the cycle on which it is administered. One of skill in the art could routinely perform empirical activity tests to determine the bioactivity of the compound in bioassays and thus determine what dosage to administer when the compound is delivered by another route.

In one embodiment, the oral dosage of the HKI-272 compound is at least about 700 mg/week. In another embodiment, the oral dosage of the HKI-272 compound is about 800 mg/week to at least to about 1700 mg/week. In another embodiment, the oral dosage of the HKI-272 compound is about 840 mg/week to about 1680 mg/week. In another embodiment, the oral dosage of the HKI-272 compound is about 900 mg/week to about 1600 mg/week. In a further embodiment, the oral dosage of the HKI-272 compound is about 1000 mg/week to about 1500 mg/week. In yet another embodiment, the oral dosage of the HKI-272 compound is about 1100 mg/week to about 1400 mg/week. In still a further embodiment, the oral dosage of the HKI-272 compound is about 1200 mg/week to about 1300 mg/week. Precise dosages are determined by the administering physician based on experience with the individual subject to be treated. Other dosage regimens and variations are foreseeable, and are determined through physician guidance.

Capecitabine may be used according to the currently approved/recommended dose of capecitabine for monotherapy of colon or breast cancer, i.e., an amount equivalent to 1250 mg/m$^2$ administered orally twice daily (equivalent to 2500 mg/m$^2$ total daily dose) for 14 days followed by a 7-day rest period given as 3-week cycles, for as long as needed. Typically the mean duration of treatment is 3 to 6 three-week cycles. The currently approved unit dosage forms are a light peach-colored film coated tablet containing 150 mg of capecitabine and a peach-colored film coated tablet containing 500 mg of capecitabine. In another embodiment, the doses of capecitabine may be reduced for use in the combination therapy of the present invention. Alternatively, high doses of capecitabine may be used for a period of one to multiple days, with reduced doses being delivered on certain days within a cycle. For example, a daily starting oral dose may be in the range of, e.g., 1250 mg to 3000 mg, 1500 mg to 4000 mg, 1500 mg to 2000 mg, 2000 mg to about 3600 mg, or about 2400 mg to about 3600 mg per day, on the days in the cycle on which it is administered. In another embodiment, the combination of the invention permits lower daily doses (subtherapeutic) of the capecitabine to be used, thus minimizing the risk of dose-limiting side effects. In one embodiment, the daily dose of capecitabine is 750 mg to 2000 mg, 900 to 1800 mg, or about 1250 mg to 1450 mg/day.

Precise dosages are determined by the administering physician based on experience with the individual subject to be treated. Other dosage regimens and variations are foreseeable, and are determined through physician guidance. In one embodiment, the capecitabine compound is administered by i.v. infusion or orally, preferably in the form of tablets or capsules.

As described herein, subtherapeutically effective amounts of the HKI-272 compound and capecitabine compound may be used to achieve a therapeutic effect when administered in combination. In one embodiment, the HKI-272 compound is provided at dosages of 5 to 50% lower when provided along with the capecitabine compound. In another embodiment, the HKI-272 compound is provided at dosages of 10 to 25% lower when provided along with the capecitabine compound. In a further embodiment, the HKI-272 compound is provided at dosages of 15 to 20% lower when provided along with the capecitabine compound. In one embodiment, a resulting HKI-272 compound dosage is about 8 to 40 mg. In another embodiment, a resulting HKI-272 compound dosage is about 8 to 30 mg. In a further embodiment, a resulting HKI-272 compound dosage is about 8 to 25 mg. Subtherapeutically effective amounts of the HKI-272 compound and capecitabine compound are expected to reduce the side-effects of treatment.

The SKI-606 compound can be administered, e.g., orally, at a dose range of about 0.01 to 600 mg/kg. In one embodiment, the SKI-606 compound is administered at a dose range of about 0.1 to about 600 mg/kg. In another embodiment, the SKI-606 compound is administered at a dose range of about 1 to about 500 mg/kg. In a further embodiment, the SKI-606 compound is administered at a dose range of about 10 to about 500 mg/kg. In yet another embodiment, the SKI-606 compound is administered at a dose range of about 100 to about 600 mg/kg. In still a further embodiment, the SKI-606 compound is administered at a dose range of about 200 to about 400 mg per day, at least about 40 mg, at least about 120 mg, or at least about 160 mg, on the days in the cycle on which it is administered. One of skill in the art could routinely perform empirical activity tests to determine the bioactivity of the compound in bioassays and thus determine what dosage to administer when the compound is delivered by another route.

In one embodiment, the oral dosage of the SKI-606 compound is at least about 1000 mg/week. In another embodiment, the oral dosage of the SKI-606 compound is about 1000 mg/week to at least to about 3000 mg/week. In another embodiment, the oral dosage of the SKI-606 compound is about 800 mg/week to about 2800 mg/week. In another embodiment, the oral dosage of the SKI-606 compound is about 800 mg/week to about 2100 mg/week. In a further embodiment, the oral dosage of the SKI-606 compound is about 1000 mg/week to about 2500 mg/week. In yet another embodiment, the oral dosage of the SKI-606 compound is about 1100 mg/week to about 2400 mg/week. In still a further embodiment, the oral dosage of the SKI-606 compound is about 1200 mg/week to about 2800 mg/week. Precise dosages are determined by the administering physician based on experience with the individual subject to be treated. Other dosage regimens and variations are foreseeable, and are determined through physician guidance.

Capecitabine may be used according to the currently approved/recommended dose of capecitabine for monotherapy of colon or breast cancer, i.e., an amount equivalent to 250-500 mg/m$^2$ administered orally twice daily (equivalent to 500-1000 mg/m$^2$ total daily dose) for 14 days followed by a 7-day rest period given as 3-week cycles, for as long as needed. Typically the mean duration of treatment is 3 to 6 three-week cycles. The currently approved unit dosage forms are a light peach-colored film coated tablet containing 150 mg of capecitabine and a peach-colored film coated tablet containing 500 mg of capecitabine. In another embodiment, the doses of capecitabine may be reduced for use in the combination therapy of the present invention. Alternatively, high doses of capecitabine may be used for a period of one to multiple days, with reduced doses being delivered on certain days within a cycle. For example, a daily starting oral dose may be in the range of, e.g., 100 mg to 1500 mg, 250 mg to 1500 mg, 500 mg to 1000 mg, 500 mg to about 2000 mg, or about 500 mg to about 3600 mg per day, on the days in the cycle on which it is administered. In another embodiment, the combination of the invention permits lower daily doses (subtherapeutic) of the capecitabine to be used, thus minimizing the risk of dose-limiting side effects. In one embodiment, the daily dose of capecitabine is 500 mg to 1000 mg, 250 to 1500 mg, or about 100 mg to 2000 mg/day.

Alternatively, one or more of the active agents in the combination described herein is to be used in a supratherapeutic amount, i.e., at a higher dosage in the combination than when used alone. In this embodiment, the other active agent(s) are used in a therapeutic or subtherapeutic amount.

In one embodiment, a regimen as provided herein is used for treating a neoplasm characterized by an erB-2 (HER-2) overexpressing neoplasm. In another embodiment, a regimen as provided herein is used for treating a neoplasm characterized by overexpression of an erB-1 overexpressing neoplasm.

In still another embodiment, a regimen as described herein is used for treating a breast cancer. In certain embodiments, the breast cancer may be an erB-2-overexpressing metastatic or locally advanced breast cancer.

In addition, the capecitabine compound/or 4-anilino-3-cyanoquinoline compound (e.g. HKI-272, SKI-606, EKB-569) may also be administered after completion of chemotherapy as maintenance therapy.

Optional Components of the Regimens

The regimens described herein may also include the administration of other active agents which are not anti-neoplastics, but which ameliorate the symptoms of the neoplastic disease and/or therapy.

In still further embodiment, the combination may include an anti diarrheal. One of skill in the art would readily be able to select a suitable antidiarrheal for use herein including, without limitation, loperamide or diphenoxylate hydrochloride and atropine sulfate. Alternatively, the anti-diarrheal may be administered to the patient prior to or subsequent to treatment with the capecitabine compound and/or the 4-anilino-3-cyanoquinoline compound (e.g. HKI-272, SKI-606, EKB-569).

In a further embodiment, the combination further contains an antiemetic agent. Examples of antiemetic agents include, without limitation, metoclopramide, Dolasetron, Granisetron, Ondansetron, Tropisetron, and Palonosetron, among others. Alternatively, the antiemetic may be administered to the patient prior to or subsequent to treatment with the capecitabine compound and/or the 4-anilino-3-cyanoquinoline compound (e.g. HKI-272, SKI-606, EKB-569).

In yet a further embodiment, the combination also contains an antihistamine. Examples of antihistamines include, without limitation, Cyclizine, Diphenhydramine, Dimenhydrinate (Gravol), Meclizine, Promethazine (Pentazine, Phenergan, Promacot), or Hydroxyzine, among others. Alternatively, the antihistamine may be administered to the patient prior to or subsequent to treatment with the capecitabine compound and/or HKI-272 compound.

In yet another embodiment, the combination may include a growth factor to prevent and/or treat neutropenia. Such growth factors may readily be selected by those skill in the art according to practice guidelines from the American Society of Clinical Oncology (ASCO; 2006). Alternatively, the growth factor may be administered to the patient prior to or subsequent to treatment with the capecitabine compound and/or the 4-anilino-3-cyanoquinoline compound (e.g. HKI-272, SKI-606, EKB-569).

In still another embodiment, the regimen may be used in combination with other anti-neoplastic agents.

As is typical with oncology treatments, dosage regimens are closely monitored by the treating physician, based on numerous factors including the severity of the disease, response to the disease, any treatment related toxicities, age, and health of the patient. Dosage regimens are expected to vary according to the route of administration.

The dosages and schedules described hereinbefore may be varied according to the particular disease state and the overall condition of the patient. For example, it may be necessary or desirable to reduce the above-mentioned doses of the components of the combination treatment in order to reduce toxicity. Dosages and schedules may also vary if, in addition to a combination of an 4-anilino-3-cyanoquinoline compound (e.g. HKI-272, SKI-606, EKB-569) and a capecitabine, one or more additional chemotherapeutic agents are used. Scheduling can be determined by the practitioner who is treating any particular patient using his professional skill and knowledge.

Pharmaceutical Packs and Kits

Also included is a product or pharmaceutical pack containing a course of an anti-neoplastic treatment for one individual mammal comprising one or more container(s) having one, one to four, or more unit(s) of the HKI-272 compound in unit dosage form and, optionally, one, one to four, or more unit(s) of the HKI-272 and capecitabine compounds, and optionally, another active agent. The combinations may be in the form of a kit of parts.

For the HKI-272 compound and/or capecitabine compound, it is desired each compound of the combination of compounds is in the form of a unit dose. The term "unit dose" or "unit dose form" as used herein describes a single dose form including, without limitation, tablets, caplets, capsules, powders in sachets or vials, saline infusion bags, as described above.

Unit dose forms contain from about 0.1 to about 300 mg of a HKI-272 compound. In another embodiment, the unit dose form contains about 5 to about 300 mg of the HKI-272 compound. In another embodiment, the unit dose form contains about 50 to about 300 mg of the HKI-272 compound. In a further embodiment, the unit dose form contains about 75 to about 300 mg of the HKI-272 compound. In still a further embodiment, the unit dose form contains about 100 to about 300 mg of the HKI-272 compound. In yet another embodiment, the unit dose form contains about 120 to about 300 mg of the HKI-272 compound. In yet a further embodiment, the unit dose form contains about 160 to about 300 mg of the HKI-272 compound. In another embodiment, the unit dose form contains about 200 to about 300 mg of the HKI-272 compound. In yet another embodiment, the unit dose form contains about 240 to about 300 mg of the HKI-272 compound. In a further embodiment, the unit dose form contains about at least about 120 mg. In still a further embodiment, the unit dose form contains at least about 160 mg. In another embodiment, the unit dose form contains at least about 240 mg.

Currently, unit doses of capecitabine are commercially available as 150 mg or 500 mg tablets under the mark XELODA®. However, other suitable unit doses may be prepared as desired or required.

The invention therefore includes administering an HKI-272 compound and capecitabine compound to a subject for the treatment of a neoplasm. In one embodiment, the HKI-272 compound is administered separately from the capecitabine compound. In a further embodiment, the HKI-272 compound is administered prior to the capecitabine compound. In another embodiment, the HKI-272 compound is administered subsequent to the capecitabine compound. In still another embodiment, the HKI-272 compound and the capecitabine compound are administered simultaneously, but separately. In one embodiment, the HKI-272 compound and the capecitabine compound are administered together as a combined preparation.

In one embodiment, a product contains an HKI-272 compound and capecitabine compound as a combined preparation for simultaneous, separate or sequential use in treating a neoplasm in a mammal in need thereof. In one embodiment, the HKI-272 compound is separately formulated from the capecitabine compound.

In one embodiment, a pharmaceutical pack contains a course of treatment of a neoplasm for one individual mammal, wherein the pack contains units of an HKI-272 compound in unit dosage form and units of a capecitabine compound in unit dosage form. In another embodiment, a pharmaceutical pack contains a course of treatment of a neoplasm for one individual mammal, wherein the pack contains units of an HKI-272 compound in unit dosage form and units of a capecitabine compound in unit dosage form. In yet another embodiment, a pharmaceutical pack as described herein contains a course of treatment of metastatic breast cancer for one individual mammal.

Also included is a product or pharmaceutical pack containing a course of an anti-neoplastic treatment for one individual mammal comprising one or more container(s) having one, one to four, or more unit(s) of the SKI-606 compound in unit dosage form and, optionally, one, one to four, or more unit(s) of the SKI-606 and capecitabine compounds, and optionally, another active agent. The combinations may be in the form of a kit of parts.

For the SKI-606 compound and/or capecitabine compound, it is desired each compound of the combination of compounds is in the form of a unit dose. The term "unit dose" or "unit dose form" as used herein describes a single dose form including, without limitation, tablets, caplets, capsules, powders in sachets or vials, saline infusion bags, as described above.

Unit dose forms contain from about 0.1 to about 600 mg of a SKI-606 compound. In another embodiment, the unit dose form contains about 5 to about 600 mg of the SKI-606 compound. In another embodiment, the unit dose form contains about 50 to about 500 mg of the SKI-606 compound. In a further embodiment, the unit dose form contains about 100 to about 500 mg of the SKI-606 compound. In still a further embodiment, the unit dose form contains about 150 to about 500 mg of the SKI-606 compound. In yet another embodiment, the unit dose form contains about 200 to about 400 mg of the SKI-606 compound. In a further embodiment, the unit dose form contains about at least about 120 mg. In still a further embodiment, the unit dose form contains at least about 160 mg. In another embodiment, the unit dose form contains at least about 200 mg.

Currently, unit doses of capecitabine are commercially available as 150 mg or 500 mg tablets under the mark XELODA®. However, other suitable unit doses may be prepared as desired or required.

The invention therefore includes administering an SKI-606 compound and capecitabine compound to a subject for the treatment of a neoplasm. In one embodiment, the SKI-606 compound is administered separately from the capecitabine compound. In a further embodiment, the SKI-606 compound is administered prior to the capecitabine compound. In another embodiment, the SKI-606 compound is administered subsequent to the capecitabine compound. In still another embodiment, the SKI-606 compound and the capecitabine compound are administered simultaneously, but separately. In one embodiment, the SKI-606 compound and the capecitabine compound are administered together as a combined preparation.

In one embodiment, a product contains an SKI-606 compound and capecitabine compound as a combined preparation for simultaneous, separate or sequential use in treating a neoplasm in a mammal in need thereof. In one embodiment, the SKI-606 compound is separately formulated from the capecitabine compound.

In one embodiment, a pharmaceutical pack contains a course of treatment of a neoplasm for one individual mammal, wherein the pack contains units of an SKI-606 compound in unit dosage form and units of a capecitabine compound in unit dosage form. In another embodiment, a pharmaceutical pack contains a course of treatment of a neoplasm for one individual mammal, wherein the pack contains units of an SKI-606 compound in unit dosage form and units of a capecitabine compound in unit dosage form. In yet another embodiment, a pharmaceutical pack as described herein contains a course of treatment of metastatic breast cancer for one individual mammal.

Administration of the individual components or a composition containing two or more of the individual components may employ any suitable route. Such routes may be selected from, e.g., oral, intravenous (i.v.), respiratory (e.g., nasal or intrabronchial), infusion, parenteral (aside from i.v., such as intralesional, intraperitoneal and subcutaneous injections), intraperitoneal, transdermal (including all administration across the surface of the body and the inner linings of bodily passages including epithelial and mucosal tissues), and vaginal (including intrauterine administration). Other routes of administration are also feasible and include, without limitation, liposome-mediated delivery, topical, nasal, sublingual, uretheral, intrathecal, ocular or otic delivery, implant, rectal, or intranasal.

While the components may be delivered via the same route, a product or pack described herein may contain a capecitabine compound for delivery by a different route than that of an 4-anilino-3-cyanoquinoline compound (e.g. HKI-272, SKI-606, EKB-569) compound, e.g., one or more of the components may be delivered orally, while the other is administered by another route. In one embodiment, the 4-anilino-3-cyanoquinoline compound (e.g. HKI-272, SKI-606, EKB-569) is prepared for oral delivery and the capecitabine compound is prepared for intravenous delivery. Optionally, other active components may be delivered by the same or different routes as the 4-anilino-3-cyanoquinoline compound (e.g. HKI-272, SKI-606, EKB-569) and/or capecitabine compounds. Other variations would be apparent to one skilled in the art.

In still another embodiment, the compounds or components of the therapeutic regimen are administered once a week. In certain situations, dosing with the 4-anilino-3-cyanoquinoline compound (e.g. HKI-272, SKI-606, EKB-569) may be delayed or discontinued for a brief period (e.g., 1, 2 or three weeks) during the course of treatment. Such a delay or discontinuation may occur once, or more, during the course of treatment. The effective amount is known to one of skill in the art; it will also be dependent upon the form of the 4-anilino-3-cyanoquinoline compound (e.g. HKI-272, SKI-606, EKB-569). One of skill in the art could routinely perform empirical activity tests to determine the bioactivity of the 4-anilino-3-cyanoquinoline compound (e.g. HKI-272, SKI-606, EKB-569) in bioassays and thus determine a suitable dosage to administer.

The 4-anilino-3-cyanoquinoline compound (e.g. HKI-272, SKI-606, EKB-569) and capecitabine compounds or other optional compounds used in the combination and products described herein may be formulated in any suitable manner. However, the amounts of each compound in the unit dose can vary widely depending on the type of composition, regimen, size of a unit dosage, kind of excipients, and other factors well known to those of ordinary skill in the art. In one embodiment, the unit dose can contain, e.g., 0.000001 percent by weight (% w) to 10% w of either compound. In another embodiment the unit dose can contain about 0.00001% w to 1% w, with the remainder being the excipient or excipients.

The compositions described herein may be in a form suitable for oral administration, e.g., tablet, caplet, capsule, buccal forms, troches, lozenges and oral liquids, suspensions or solutions; parenteral injection (including intravenous, subcutaneous, intramuscular, intravascular or infusion), e.g., as a sterile solution, suspension or emulsion; topical administration, e.g., an ointment or cream; rectal administration, e.g., a suppository; or the route of administration may be by direct injection into the tumor or by regional delivery or by local delivery. In other embodiments, one or both components of the combination treatment may be delivered endoscopically, intratracheally, intralesionally, percutaneously, intravenously, subcutaneously, intraperitoneally or intratumorally. In general the compositions described herein may be prepared in a conventional manner using conventional excipients or carriers that are well known in the art. Pharmaceutical compositions for oral use may also be in the form of hard gelatin capsules in which the active ingredient is mixed with an inert solid excipient, e.g., calcium carbonate, calcium phosphate or kaolin, or as soft gelatin capsules in which the active ingredient is mixed with water or an oil, such as peanut oil, liquid paraffin or olive oil. In one embodiment, one or both of said capecitabine compound and said 4-anilino-3-cyanoquinoline compound (e.g. HKI-272, SKI-606, EKB-569) are delivered orally to said subject.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet or caplet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

Oral formulations herein, e.g., tablets, caplets, or capsules described above, may utilize standard delay or time release formulations to alter the absorption of the active compound(s). The oral formulation may also consist of administering the active ingredient in water or a fruit juice, containing appropriate solubilizers or emulsifiers as needed.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol and liquid polyethylene glycol), suitable mixtures thereof, and vegetable oils. Preferred injectable formulations containing capecitabine are described in the art. In one embodiment, the compounds may be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations may contain a preservative to prevent the growth of microorganisms. In one embodiment, one or both of the capecitabine and HKI-272 compounds are delivered intravenously.

For use herein, transdermal administrations include all administrations across the surface of the body and the inner linings of bodily passages including epithelial and mucosal tissues. Such administrations may be performed using the present compounds, or pharmaceutically acceptable salts thereof, in lotions, creams, foams, patches, suspensions, solutions, and suppositories (rectal and vaginal). Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

In another embodiment, one or both of the 4-anilino-3-cyanoquinoline compound (e.g. HKI-272, SKI-606, EKB-569) and capecitabine compounds can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of one or more compound into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). In other cases, the preferred preparation of one or more of the components can be a lyophilized powder.

Encapsulating materials can also be employed with one or more of the compounds and the term "composition" can include the active ingredient in combination with an encapsulating material as a formulation, with or without other carriers. For example, the compounds can also be delivered as microspheres for slow release in the body. In one embodiment, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao, *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months. Cachets can also be used in the delivery of the compounds of the present invention, e.g., anti-atherosclerotic medicaments.

In one embodiment a kit includes a first container with a suitable composition containing a HKI-272 compound and a second container with a suitable composition containing a capecitabine compound. Accordingly, there is provided a kit for use in the treatment or prophylaxis of cancer. This kit includes comprising: a) HKI-272 compound together with a pharmaceutically-acceptable excipient or carrier, in a first unit dosage form; b) a capecitabine compound together with a pharmaceutically-acceptable excipient or carrier, in a second unit dosage form; and c) a container for containing said first and second dosage forms.

In another embodiment, pharmaceutical packs contain a course of anti-neoplastic treatment for one individual mammal comprising a container having a unit of a HKI-272 compound in unit dosage form, a containing having a unit of a capecitabine compound, and optionally, a container with another active agent.

In a separate embodiment a kit includes a first container with a suitable composition containing a SKI-606 compound and a second container with a suitable composition containing a capecitabine compound. Accordingly, there is provided a kit for use in the treatment or prophylaxis of cancer. This kit includes comprising: a) SKI-606 compound together with a pharmaceutically-acceptable excipient or carrier, in a first unit dosage form; b) a capecitabine compound together with a pharmaceutically-acceptable excipient or carrier, in a second unit dosage form; and c) a container for containing said first and second dosage forms.

In some embodiments, the compositions are in packs in a form ready for administration. In other embodiments, the compositions are in concentrated form in packs, optionally with the diluent required to make a final solution for administration. In still other embodiments, the product contains a compound described herein in solid form and, optionally, a separate container with a suitable solvent or carrier.

In still other embodiments, the above packs/kits include other components, e.g., instructions for dilution, mixing and/or administration of the product, other containers, syringes, needles, etc. Other such pack/kit components are readily apparent to one of skill in the art.

In addition to the optional chemotherapeutic agents and optional compounds noted above, the regimens and methods described herein can be performed prior to, concurrently with, or subsequent to other non-medication procedures. In one embodiment, radiation may be performed prior to, concurrently with, or subsequent to treatment with the 4-anilino-3-cyanoquinoline compound (e.g. HKI-272, SKI-606, EKB-569) and capecitabine compounds.

In a further embodiment, a product containing capecitabine and a 4-anilino-3-cyanoquinoline compound (e.g. HKI-272, SKI-606, EKB-569) is provided. The product is useful as a combined preparation for simultaneous, separate or sequential use in treating a neoplasm in a mammal.

In still a further embodiment, a pharmaceutical pack for treating a neoplasm in one individual mammal is provided. The pharmaceutical pack contains at least one unit of capecitabine and at least one unit of a 4-anilino-3-cyanoquinoline compound (e.g. HKI-272, SKI-606, EKB-569).

In another embodiment, a pharmaceutical composition is provided and contains capecitabine, a 4-anilino-3-cyanoquinoline compound (e.g. HKI-272, SKI-606, EKB-569), and at least one pharmaceutically acceptable carrier. Desirably, the pharmaceutical composition is useful for treating a neoplasm in a mammal.

In still another embodiment, a method of treating a neoplasm associated with overexpression or amplification of HER-2 in a mammal in need thereof is provided. The method includes administering a unit dose of a capecitabine compound and administering a unit dose of a 4-anilino-3-cyanoquinoline compound (e.g. HKI-272, SKI-606, EKB-569). In one embodiment, to identify subject patients for treatment according to the methods of the invention, accepted screening methods are employed to determine risk factors associated with a targeted or suspected disease or condition or to determine the status of an existing disease or condition in a subject. These screening methods include, e.g., conventional work-ups to determine risk factors that are associated with the targeted or suspected disease or condition. These and other routine methods allow the clinician to select patients in need of therapy using the methods and formulations of the present invention. In one embodiment, the "individual", "subject" or "patient" may have had no previously chemotherapeutic treatment. In another embodiment, the "individual", "subject" or "patient" may have previously undergone chemotherapeutic treatment. In another embodiment, the "individual", "subject" or "patient" may have previously been administered an aniloquinazoline class inhibitor. In a further embodiment, the "individual", "subject" or "patient" may have previously been administered lapatinib or geftinib as the aniloquinazoline class inhibitor. Desirably, the blood count of the patient prior to treatment with the described combinations is stable enough to permit administration of the combinations described herein. In one embodiment, the neutrophil count of the patient prior to administration of the capecitabine and 4-anilino-3-cyanoquinoline (e.g. HKI-272, SKI-606, EKB-569) compounds is at least 1500. In another embodiment, the platelet count of the patient prior to administration of the capecitabine and 4-anilino-3-cyanoquinoline (e.g. HKI-272, SKI-606, EKB-569) compounds is at least 100,000/L.

The following examples illustrate of the uses of the combinations of the invention. It will be readily understood that alterations or modifications, e.g., in the formulation of the components, the routes of delivery, and the dosing, can be made for reasons known to those of skill in the art.

EXAMPLES

The combination of lapatinib and capecitabine has been chosen as the comparator therapy in this study due to recent approval by the FDA for the treatment of subjects with advanced or metastatic breast cancer whose tumors overexpress erbB-2 and who have received prior therapy including an anthracycline, a taxane, and trastuzumab. The registration trial indicated an ORR of 24% and median TTP of 27 weeks for the combination of both drugs (per independent review).

Preliminary pharmacokinetic (PK) analyses demonstrated that neratinib absorption was relatively slow, and the maximum concentration ($C_{max}$) was generally attained within 3 to 6 hours. After oral administration, the neratinib $C_{max}$ and area under the concentration-versus-time curve (AUC) increased in a dose-dependent manner in general. Mean steady-state $C_{max}$ and AUC values were 70.1 ng/mL and 975 ng.h/mL for the 180-mg dose group, respectively, 73.5 ng/mL and 939 ng·h/mL for the 240-mg dose group, respectively, 90.4 ng/mL and 1333 ng·h/mL for the 320-mg dose group, respectively, and 105 ng/mL and 1704 ng·h/mL for the highest dose of 400 mg, respectively. The neratinib exposure (AUC) increased 1.2- to 2.7-fold (mean accumulation ratio) when comparing the steady-state exposure on day 21 after repeated daily administration with the exposure on day 1 after administration of 80 to 400 mg of neratinib. The mean accumulation ratio was 1.2 after a 240-mg dose, indicating no significant accumulation of neratinib after repeated daily dose administration at the dose to be used in this proposed trial.

The data indicated a slow distribution of neratinib with a large apparent volume of distribution ($V_z/F$ on day 1: about 3188 to 6181 L) after oral absorption. After oral administration on day 1, neratinib was eliminated with a mean apparent terminal half-life ($t_{1/2}$) of approximately 13 to 17 hours. There was moderate to large variability in neratinib $t_{1/2}$, $C_{max}$, and AUC; coefficients of variation (CVs) generally ranged from 8% to 90%.

In an ongoing phase 2 study, neratinib is being administered as daily oral doses of 240 mg in subjects with erbB-2-overexpressing advanced or metastatic breast cancer, who received up to 4 prior cytotoxic chemotherapy treatment regimens, with prior trastuzumab therapy for metastatic or locally advanced disease (≥6 weeks) or with no prior exposure to erbB-2-targeted treatment. Preliminary results were obtained for 124 subjects evaluable for efficacy based on independent assessment and 131 subjects evaluable per investigator assessment. For subjects with prior trastuzumab containing therapy in the metastatic setting, the ORR was 26% (95% CI: 16-39%; independently assessed) and 35% (95% CI: 23-47%; investigator assessed), while an ORR of 51% (95% CI: 38-64%; independently assessed) and 62% (95% CI: 49-74%; investigator assessed) was observed in trastuzumab naïve subjects. Median Progression Free Survival (PFS) for independent (and investigator) assessment was 23 (22), with a 16-week PFS rate of 61% (57%) in subjects who had received prior trastuzumab. For trastuzumab naïve subjects, PFS per independent (and investigator) assessment was 40 (35), with a 16-week PFS rate of 75% (78%).

The predominant AE was diarrhea, which was reversible and generally manageable by medication, temporary discontinuation of treatment, or dose reduction. Diarrhea that was considered related to neratinib occurred with a frequency of 94% of the subjects. Of those, grade 3-4 diarrhea was experienced by 25% of the subjects. Other common AEs were nausea (related to neratinib in 30%, grade 3-4 in 2% of the subjects), vomiting (related in 23%, grade 3-4 in 2%), fatigue (related in 20%, grade 3-4 in <2%), and anorexia (related in 16%, grade 3-4 in 4%). These data show that daily oral doses of 240 mg of neratinib are generally well tolerated, and neratinib has significant antitumor activity in subjects with erbB-2-positive advanced breast cancer [Burstein, H J, Awada A, Badwe R, et al. 2007. Presented at the Poster presented at the SABCS, San Antonio, USA].

Example 1

Anti-tumor Activity of Neratinib (HKI-272) and Capecitabine Combination

Subjects with solid tumors will be enrolled in each dose group of the combination of neratinib and capecitabine. Each subject will participate in only 1 dose group. For the purpose of this study, a cycle is defined as a 21-day period.

Each subject will participate at only 1 dose level. Subjects will receive oral neratinib tablets (160 or 240 mg) daily in combination with oral capecitabine (750 or 1000 mg/m$^2$ BID (twice daily)) on days 1-14 of a 21-day cycle (no capecitabine administered days 15-21). For comparative purposes, lapatinib [TYKERB®] is administered orally once daily continuously according to manufacture's instruction.

| Dose level | Neratinib dose (mg) Continuous daily oral dosing | Capecitabine dose (mg/m$^2$) BID Days 1-14 of each 21-day cycle |
|---|---|---|
| 1 | 160 | 750 (total 1500 daily) |
| 2 | 240 | 750 (total 1500 daily) |
| 3 | 240 | 1000 (total 2000 daily) |

If dose level 1 is not tolerated, Part 2 will proceed with 2 arms: A (neratinib) and C (lapatinib+capecitabine).

If dose level 1 is tolerated but dose level 2 is not tolerated, an intermediate dose level at 200 mg of neratinib in combination with 750 mg/m$^2$ BID capecitabine may be investigated for MTD.

Dose delays and adjustments will be permitted. All subjects are allowed a maximum of 3 consecutive weeks dose delay to allow for toxicities to resolve.

As used herein, a complete response (CR) refers to the disappearance of all target lesions. A partial response (PR) refers to an at least 30% decrease in the sum of the longest diameter (LD), taking as reference the baseline sum LD. Stable disease is defined as having neither sufficient shrinkage to qualify for PR nor sufficient increase to qualify for PD, taking as reference the smallest sum LD since treatment started.

Example 2

HKI-272+Capecitabine in erbB-2 Positive Breast Cancer

Patients having diagnosed metastatic breast cancers are treated using a regimen of HKI-272 and capecitabine for three 21-day cycles. Control groups include patients who will receive oral HKI-272 monotherapy (240 mg daily) (Group 1) or a combination of lapatinib [TYKERB®, oral 1250 mg daily] and capecitabine [XELODA®, oral 2000 mg daily] (Group 2) according to manufacturer recommendations.

Patients receive oral HKI-272 tablets (either 160 mg or 240 mg) daily in combination with oral capecitabine (either 750 mg or 1000 mg twice daily) on days 1-14 of a 21-day cycle (no capecitabine administered days 15-21). Oral dosing of HKI-272 begins at cycle 1 and continues on the remaining days of the each cycle.

It is anticipated that results will show that HKI-272 in combination with capecitabine will significantly improve objective response rate as compared to the combination of lapatinib and capecitabine and/or prolonged subject's time to tumor progression (TTP) when compared to capecitabine monotherapy. It is further anticipated that side effects will be minimized as compared to the combination of lapatinib and capecitabine, in view of the lower effective dosages permitted by the combination of HKI-272 and capecitabine.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

Example 3

Anti-tumor Activity of Bosutinib (SKI-606) and Capecitabine Combination

Subjects with solid tumors will be enrolled in each dose group of the combination of bosutinib and capecitabine. Each subject will participate in only 1 dose group. For the purpose of this study, a cycle is defined as a 21-day period.

Each subject will participate at only 1 dose level. Subjects will receive oral bosutinib tablets (200-400 mg) daily in combination with oral capecitabine (500-1000 mg/m$^2$ BID (twice daily)) on days 1-14 of a 21-day cycle (no capecitabine administered days 15-21). For comparative purposes, lapatinib [TYKERB®] is administered orally once daily continuously according to manufacture's instruction.

| Dose level | Bosutinib dose (mg) Continuous daily oral dosing | Capecitabine dose (mg/m$^2$) BID Days 1-14 of each 21-day cycle |
|---|---|---|
| 1 | 200 | 250 (total 500 daily) |
| 2 | 300 | 300 (total 600 daily) |
| 3 | 400 | 500 (total 1000 daily) |

If dose level 1 is not tolerated, Part 2 will proceed with 2 arms: A (bosutinib) and C (lapatinib+capecitabine).

If dose level 1 is tolerated but dose level 2 is not tolerated, an intermediate dose level at 200 mg of bosutinib in combination with 750 mg/m$^2$ BID capecitabine may be investigated for MTD.

Dose delays and adjustments will be permitted. All subjects are allowed a maximum of 3 consecutive weeks dose delay to allow for toxicities to resolve.

As used herein, a complete response (CR) refers to the disappearance of all target lesions. A partial response (PR) refers to an at least 30% decrease in the sum of the longest diameter (LD), taking as reference the baseline sum LD. Stable disease is defined as having neither sufficient shrinkage to qualify for PR nor sufficient increase to qualify for PD, taking as reference the smallest sum LD since treatment started.

Example 4

SKI-606+Capecitabine in erbB-2 Positive Breast Cancer

Patients having diagnosed metastatic breast cancers are treated using a regimen of SKI-606 and capecitabine for three 21-day cycles. Control groups include patients who will receive oral SKI-606 monotherapy (200-400 mg daily) (Group 1) or a combination of lapatinib [TYKERB®, oral 1250 mg daily] and capecitabine [XELODA®, oral 1000 mg daily] (Group 2) according to manufacturer recommendations.

Patients receive oral SKI-600 tablets (either 200 mg or 400 mg) daily in combination with oral capecitabine (either 250 mg or 500 mg twice daily) on days 1-14 of a 21-day cycle (no capecitabine administered days 15-21). Oral dosing of SKI-606 begins at cycle 1 and continues on the remaining days of the each cycle.

It is anticipated that results will show that SKI-606 in combination with capecitabine will significantly improve objective response rate as compared to the combination of lapatinib and capecitabine and/or prolonged subject's time to tumor progression (TTP) when compared to capecitabine monotherapy. It is further anticipated that side effects will be minimized as compared to the combination of lapatinib and capecitabine, in view of the lower effective dosages permitted by the combination of SKI-606 and capecitabine.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A method for treating an ErbB-2 positive metastatic breast cancer in a subject; comprising administering to the subject neratinib and capecitabine; wherein neratinib and capecitabine act synergistically.

2. The method of claim 1, wherein the breast cancer is a locally advanced breast cancer.

3. The method according to claim 1, wherein one or both of capecitabine and neratinib is administered in a subtherapeutically effective amount.

4. The method according to claim 1, wherein neratinib and capecitabine are administered orally.

5. The method according to claim 1, wherein neratinib and capecitabine are administered concurrently, sequentially, simultaneously, in a specified order, or according to a specific temporal relationship.

6. The method according to claim 1, wherein neratinib is administered in a unit dose.

7. The method according to claim 6, wherein capecitabine is administered in a unit dose.

8. The method according to claim 1, wherein capecitabine is administered in an amount of about 1250 mg to about 3000 mg daily.

9. The method according to claim 1, wherein capecitabine is administered at least once over a period of 21 days.

10. The method according to claim 1, wherein the administration of capecitabine is continued for 3 to 6 cycles.

11. The method according to claim 1, wherein neratinib is administered in an amount of at least 40 mg per day.

12. The method according to claim 11, wherein neratinib is administered in an amount of at least 120 mg per day.

13. The method according to claim 12, wherein neratinib is administered in an amount of at least 240 mg per day.

14. The method according to claim 1, wherein neratinib is administered daily.

15. The method according to claim 1, wherein neratinib is administered at least once daily.

16. The method according to claim 1, wherein neratinib is administered for at least 2 continuous weeks.

17. The method according to claim 1, wherein neratinib is administered before capecitabine.

18. The method according to claim 1, wherein neratinib is administered after capecitabine.

19. The method according to claim 1, wherein neratinib and capecitabine are administered simultaneously.

20. The method according to claim 1, wherein administration of capecitabine is discontinued after about 24 weeks.

21. The method of claim 1, wherein neratinib is administered in a dose range of about 20 to about 240 mg per day.

22. The method of claim 1, wherein the subject is a human.

23. A method for treating an ErbB-2 positive metastatic breast cancer in a subject, wherein one treatment cycle comprises 21 days, comprising:
  (a) orally administering to the subject at least one unit dose of neratinib daily starting on day 1 of said cycle; and
  (b) orally administering to the subject at least one a unit dose of capecitabine on days 1 to 14 of said cycle;
  wherein neratinib and capecitabine act synergistically.

* * * * *